US00PP12648P2

(12) United States Plant Patent
Oudshoorn

(10) Patent No.: US PP12,648 P2
(45) Date of Patent: May 28, 2002

(54) RUDBECKIA PLANT NAMED 'BLACK BEAUTY'

(75) Inventor: Herbert Oudshoorn, Rypwetering (NL)

(73) Assignee: Future Plants V.O.F., Noordwijk (NL)

( * ) Notice: Subject to any disclaimer, the term of this patent is extended or adjusted under 35 U.S.C. 154(b) by 0 days.

(21) Appl. No.: 09/473,560

(22) Filed: Dec. 29, 1999

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Rudbeckia plant named 'Black Beauty', characterized by its upright plant habit; relatively small inflorescences; and disc florets that are almost black with golden yellow pollen.

2 Drawing Sheets

BACKGROUND OF THE INVENTION

The present invention relates to a new and distinct cultivar of Rudbeckia plant, botanically known as *Rudbeckia occidentalis,* and hereinafter referred to by the cultivar name Black Beauty.

The new cultivar is a product of a planned breeding program conducted by the Inventor in Rypwetering, The Netherlands. The objective of the breeding program was to develop new Rudbeckia cultivars with small inflorescences with black-colored disc florets that develop uniformly.

The new cultivar originated from a cross made by the Inventor in 1994 of two unidentified seedling selections of *Rudbeckia occidentalis.*

The cultivar Black Beauty was discovered and selected by the Inventor as a flowering plant within the progeny of the stated cross in a controlled environment in Rypwetering, The Netherlands.

Asexual propagation of the new cultivar by divisions harvested at Rypwetering, The Netherlands, has shown that the unique features of this new Rudbeckia are stable and reproduced true to type in successive generations.

SUMMARY OF THE INVENTION

The following traits have been repeatedly observed and are determined to be the unique characteristics of 'Black Beauty'. These characteristics in combination distinguish 'Black Beauty' as a new and distinct cultivar:

1 1. Upright plant habit.

1 2. Relatively small inflorescences.

1 3. Disc florets that are almost black with golden yellow pollen.

Plants of the cultivar Black Beauty have not been observed under all possible environmental conditions. The phenotype may vary somewhat with variations in environment such as temperature, light intensity, daylength, and fertility level without, however, any variance in genotype.

Plants of the new Rudbeckia are smaller, have glossier leaves and more uniform disc floret development than plants of both parent seedling selections.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Rudbeckia.

The photograph on the first sheet comprises a side perspective view of typical plants of the new Rudbeckia.

The photograph at the top of the second sheet comprises a close-up view of a typical inflorescence of the new Rudbeckia.

The photograph at the bottom of the second sheet comprises a close-up view of typical leaves and an inflorescence of the new Rudbeckia. Plants used for the photographs were about one year old.

DETAILED BOTANICAL DESCRIPTION

In the following description, color references are made to The Royal Horticultural Society Colour Chart except where general terms of ordinary dictionary significance are used. Plants used for the description were about one year-old and grown in 17-cm containers under outdoor production conditions which closely approximate commercial production conditions during the spring and summer in Rypwetering, The Netherlands.

Botanical classification: *Rudbeckia occidentalis* cultivar Black Beauty.

Parentage:

*Female parent.*—Unidentified seedling selection of *Rudbeckia occidentalis.*

*Male parent.*—Unidentified seedling selection of *Rudbeckia occidentalis.*

Propagation:

*Type.*—By root divisions.

*Time to initiate roots.*—About four weeks in the spring.

*Rooting habit.*—Fine.

Plant description:

*Appearance.*—Perennial herbaceous container and garden plant. Erect and upright growth habit; narrow inverted triangle.

*Crop time.*—From planting rooted cuttings, about 30 to 35 weeks are required to produce a finished plant.

*Vigor.*—Moderate to vigorous.

*Plant height.*—About 1.2 meters.

*Plant spread.*—About 45 cm.

*Lateral branch description.*—Quantity: About one or two per basal stem. Length: About 12 cm. Diameter: About 2.5 mm. Inernode length: About 4 mm. Texture: Longitudinal ribbed. Color: 137C.

*Foliage description.*—Leaves alternate, single; durable. Length, fully expanded leaves, basal: About 13 cm. Width, fully expanded leaves, basal: About 6.5 cm. Shape: Narrowly ovate. Apex: Acute. Base: Attenuate. Margin: Entire. Texture: Very sparsely covered with short (less than 0.5 mm) gray-green hairs along the midvein on the lower surface. Color: Young and mature leaves, upper surface: 139A. Young and mature leaves, lower surface: 137C. Venation, upper surface: Midvein, 138D; lateral veins, 139A. Venation, lower surface: Midvein, 138C to 138D; lateral veins, 137C. Petiole: Length: About 2 cm. Diameter: About 4 mm. Color: 137C to 155D.

Inflorescence description:

*Appearance.*—Composite inflorescence form lacking ray florets. Disc florets arranged acropetally on a capitulum. Inflorescences displayed above the foliage; one to three inflorescences per lateral stem; peduncles arising from leaf axils. Inflorescences last about 8 weeks on the plant and about 2 to 3 weeks as cut flowers. Disc florets self-cleaning.

*Flowering response.*—Plants flower continuously from summer to fall.

*Fragrance.*—Faint, dull; slightly unpleasant.

*Inflorescence size.*—Diameter: About 2.3 cm. Depth (height): About 4 cm.

*Inflorescence bud* (*just before florets open*).—Length: About 2.5 cm. Diameter: About 1.8 cm. Shape: Ovoid. Color: Almost black, close to 202A.

*Disc florets.*—Shape: Tubular. Length: About 4.5 mm. Width: About 0.8 mm. Color: Immature: Base and mid-section, 138D or paler; apex, almost black, close to 202A. Mature: Base and mid-section, 138D or paler to 142A; apex, almost black, close to 202A.

*Phyllaries.*—Length: About 1.7 cm. Shape: Ensiform. Apex: Acute. Margin: Entire. Quantity and arrangement: About 14 to 16 per inflorescence. Texture: Smooth; longitudinally ribbed. Color: Upper surface: 137B to 137C. Lower surface: 137C to 137D.

*Peduncle.*—Length, from uppermost leaf to base of phyllaries: About 13 cm. Aspect: Rigid, straight, strong; inflorescences held above foliage. Color: 137C.

*Reproductive organs.*—Androecium: Stamens: Five; basifixed. Anther size: Smaller than 0.5 mm. Anther color: Almost black, close to 202A. Pollen amount: Moderate to abundant. Pollen color: Dark yellow, 15A. Gynoecium: Pistils: Two. Pistil length: About 5 mm. Stigma color: Almost black, close to 202A. Style length: About 4 mm. Style color: 142A. Ovary color: 142A.

*Seed.*—Length: About 2 mm. Diameter: About 1 mm. Color: Almost black, close to 202A.

Disease resistance: Plants of the new Rudbeckia are slightly susceptible to pathogens common to Rudbeckia.

It is claimed:

1. A new and distinct cultivar of Rudbeckia plant named 'Black Beauty', as illustrated and described.

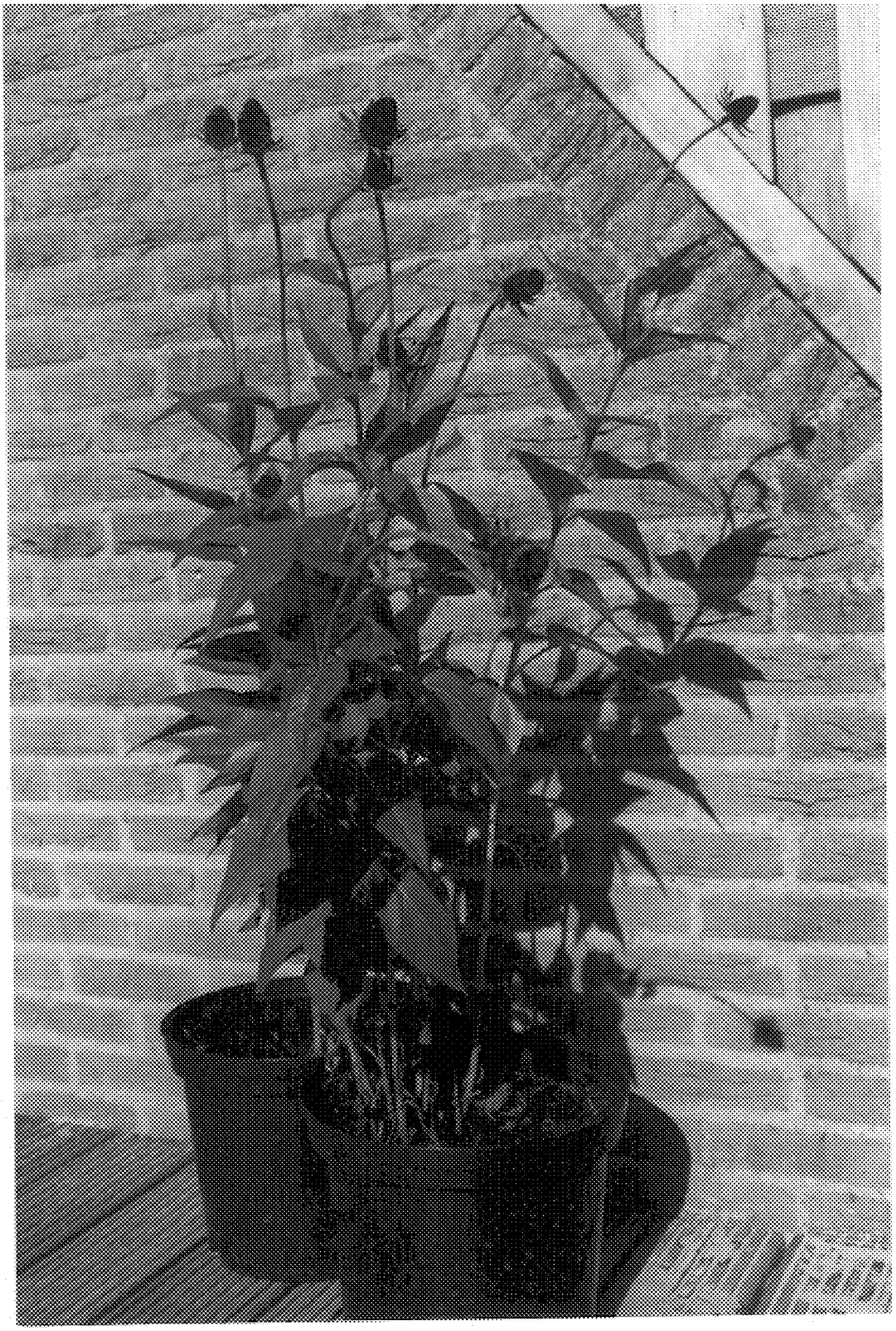

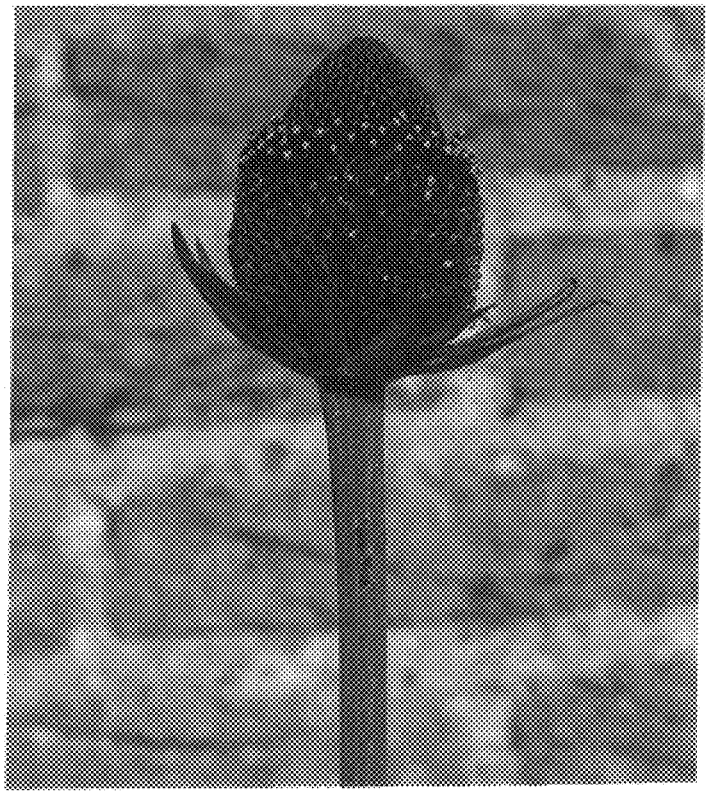
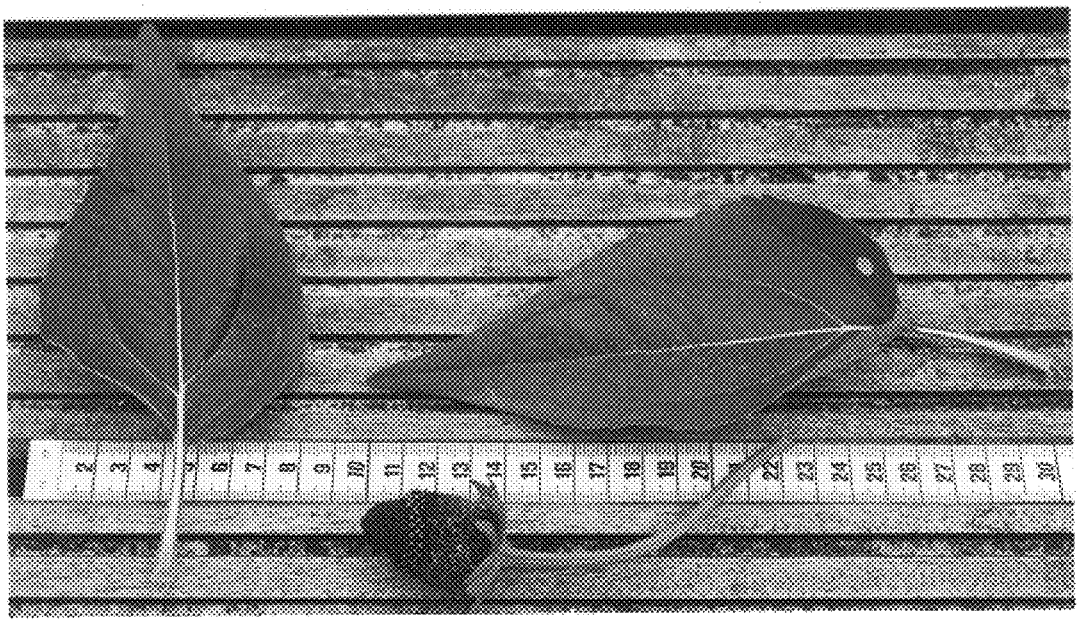

* * * * *